(12) United States Patent
Begg

(10) Patent No.: US 11,160,600 B2
(45) Date of Patent: Nov. 2, 2021

(54) MONOPOLAR RETURN ELECTRODE GRASPER WITH RETURN ELECTRODE MONITORING

(71) Applicant: COVIDIEN LP, Mansfield, MA (US)

(72) Inventor: Nikolai D. Begg, Wayland, MA (US)

(73) Assignee: Covidien LP, Mansfield, MA (US)

( * ) Notice: Subject to any disclaimer, the term of this patent is extended or adjusted under 35 U.S.C. 154(b) by 448 days.

(21) Appl. No.: 15/908,890

(22) Filed: Mar. 1, 2018

(65) Prior Publication Data

US 2019/0269451 A1  Sep. 5, 2019

(51) Int. Cl.
*A61B 18/14* (2006.01)
*A61B 18/16* (2006.01)
(Continued)

(52) U.S. Cl.
CPC ...... *A61B 18/1206* (2013.01); *A61B 18/1233* (2013.01); *A61B 18/14* (2013.01);
(Continued)

(58) Field of Classification Search
CPC . A61B 18/1206; A61B 18/16; A61B 18/1233; A61B 18/14; A61B 2018/165;
(Continued)

(56) References Cited

U.S. PATENT DOCUMENTS

D223,367 S    4/1972  Kountz
D263,020 S    2/1982  Rau, III
(Continued)

FOREIGN PATENT DOCUMENTS

CN    1103807 A    6/1995
DE    390937 C    3/1924
(Continued)

OTHER PUBLICATIONS

LigaSureTM Vessel Sealing System, the Seal of Confidence in General, Gynecologic, Urologic, and Laparoscopic Surgery, Sales/Product Literature, Jan. 2004.
(Continued)

*Primary Examiner* — Linda C Dvorak
*Assistant Examiner* — Nils A Potter
(74) *Attorney, Agent, or Firm* — Carter, DeLuca & Farrell LLP

(57) ABSTRACT

An electrosurgical system includes a generator, a delivery device, a return device, and a return electrode monitor (REM). The delivery device is in electrical communication with the generator and has a delivery electrode configured to deliver electrosurgical energy to tissue. The return device has a first jaw member including a first return electrode and a second jaw member including a second return electrode. The first and second jaw members are configured to capture tissue between the first and second return electrodes. The REM is disposed within the generator and is in electrical communication with the first and second return electrodes. The REM is configured to determine a size of a return contact area of the first and second return electrodes with tissue to prevent delivery of electrosurgical energy from the generator to tissue when the size of the return contact are is below a threshold size.

18 Claims, 4 Drawing Sheets

(51) Int. Cl.
*A61B 18/12* (2006.01)
*A61B 18/00* (2006.01)

(52) U.S. Cl.
CPC .... *A61B 18/16* (2013.01); *A61B 2018/00875* (2013.01); *A61B 2018/126* (2013.01); *A61B 2018/1253* (2013.01); *A61B 2018/165* (2013.01)

(58) Field of Classification Search
CPC .. A61B 2018/00875; A61B 2018/1253; A61B 2018/126; A61B 18/12; A61B 18/1442; A61B 2018/1467; A61B 2018/00702
USPC .......................................................... 606/35
See application file for complete search history.

(56) References Cited

U.S. PATENT DOCUMENTS

| | | | |
|---|---|---|---|
| D266,842 S | 11/1982 | Villers et al. | |
| 4,416,277 A | 11/1983 | Newton et al. | |
| D278,306 S | 4/1985 | McIntosh | |
| 4,583,556 A | 4/1986 | Hines et al. | |
| D295,893 S | 5/1988 | Sharkany et al. | |
| D295,894 S | 5/1988 | Sharkany et al. | |
| D354,218 S | 1/1995 | Van de Peer | |
| D424,693 S | 5/2000 | Pruter | |
| D424,694 S | 5/2000 | Tetzlaff et al. | |
| D425,201 S | 5/2000 | Tetzlaff et al. | |
| D449,886 S | 10/2001 | Tetzlaff et al. | |
| D457,958 S | 5/2002 | Dycus et al. | |
| D457,959 S | 5/2002 | Tetzlaff et al. | |
| D487,039 S | 2/2004 | Webster et al. | |
| D496,997 S | 10/2004 | Dycus et al. | |
| D499,181 S | 11/2004 | Dycus et al. | |
| 7,001,381 B2* | 2/2006 | Harano .............. A61B 18/1206 128/898 |
| D525,361 S | 7/2006 | Hushka | |
| 7,101,369 B2 | 9/2006 | van der Welde | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al. | |
| D564,662 S | 3/2008 | Moses et al. | |
| D576,932 S | 9/2008 | Strehler | |
| D594,736 S | 6/2009 | Esjunin | |
| D594,737 S | 6/2009 | Kelly et al. | |
| D606,203 S | 12/2009 | Husheer et al. | |
| 7,637,907 B2 | 12/2009 | Blaha | |
| D613,412 S | 4/2010 | DeCarlo | |
| 7,875,024 B2 | 1/2011 | Turovskiy et al. | |
| D634,010 S | 3/2011 | DeCarlo | |
| 8,221,412 B2* | 7/2012 | Young .............. A61B 18/1477 606/41 |
| D681,810 S | 5/2013 | DeCarlo | |
| 9,439,730 B2 | 9/2016 | Rossetto | |
| 9,549,775 B2 | 1/2017 | Dumbauld et al. | |
| 2002/0058933 A1 | 5/2002 | Christopherson et al. | |
| 2004/0049254 A1 | 3/2004 | Longo | |
| 2005/0015081 A1 | 1/2005 | Turovskiy et al. | |
| 2006/0224150 A1 | 10/2006 | Arts et al. | |
| 2007/0049916 A1* | 3/2007 | Isaacson .............. A61B 18/16 606/32 |
| 2007/0083195 A1* | 4/2007 | Werneth ............ A61B 18/1492 606/41 |
| 2009/0157071 A1* | 6/2009 | Wham .................. A61B 90/96 606/33 |
| 2009/0248019 A1* | 10/2009 | Falkenstein ...... A61B 17/07207 606/42 |
| 2010/0241023 A1 | 9/2010 | Gilbert | |
| 2013/0165923 A1* | 6/2013 | Mathur ................. A61B 18/16 606/41 |
| 2014/0364844 A1* | 12/2014 | Van Wyk ........... A61B 18/1477 606/37 |
| 2015/0126998 A1* | 5/2015 | Batchelor .......... A61B 18/1445 606/42 |
| 2015/0320478 A1 | 11/2015 | Cosman, Jr. et al. | |
| 2017/0135744 A1 | 5/2017 | Smith et al. | |
| 2019/0059991 A1* | 2/2019 | Shelton, IV ........... A61B 18/14 |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10217281 A1 | 10/2003 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102009015699 A1 | 5/2010 |
| EP | 0246350 A1 | 11/1987 |
| EP | 0521264 A2 | 1/1993 |
| EP | 0556705 A1 | 8/1993 |
| EP | 0558429 A1 | 9/1993 |
| EP | 0648515 A1 | 4/1995 |
| EP | 0836868 A2 | 4/1998 |
| EP | 0882955 A1 | 12/1998 |
| EP | 1159926 A3 | 3/2003 |
| EP | 2283788 A1 | 2/2011 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 56161636 | 12/1981 |
| JP | 5958933 | 4/1984 |
| JP | 55106 | 1/1993 |
| JP | 508933 | 2/1993 |
| JP | 0540112 | 2/1993 |
| JP | 06343644 A | 12/1994 |
| JP | 07265328 A | 10/1995 |

(56) References Cited

FOREIGN PATENT DOCUMENTS

| | | |
|---|---|---|
| JP | H0856955 | 5/1996 |
| JP | 08252263 A | 10/1996 |
| JP | 09000492 A | 1/1997 |
| JP | H0910223 A | 1/1997 |
| JP | 9117456 | 5/1997 |
| JP | 11244298 A | 9/1999 |
| JP | 2000342599 A | 12/2000 |
| JP | 2000350732 A | 12/2000 |
| JP | 2001003776 A | 1/2001 |
| JP | 2001008944 A | 1/2001 |
| JP | 2001029356 A | 2/2001 |
| JP | 2001037775 A | 2/2001 |
| JP | 2001128990 A | 5/2001 |
| JP | 2001231870 A | 8/2001 |
| JP | 2002253569 A | 9/2002 |
| JP | 2008142467 A | 6/2008 |
| KR | 20070093068 A | 9/2007 |
| KR | 20100014406 A | 2/2010 |
| KR | 20120055063 A | 5/2012 |
| SU | 166452 | 1/1965 |
| SU | 401367 A1 | 10/1973 |
| SU | 727201 A2 | 4/1980 |
| WO | 0036985 A2 | 6/2000 |
| WO | 2010035831 A1 | 4/2010 |

OTHER PUBLICATIONS

Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" INT'L Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSureTM Vessel Sealing System and LigaSureTM Atlas 20 cm Open Instrument" Innovations That Work, Jun. 2003.
Muller et al., "Extended Left Hemicolectomy Using the LigaSureTM Vessel Sealing System" Innovations That Work. LJ, Sep. 1999.
Murakami, R et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences-Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.

Palazzo et al., "Randomized clinical trial of LigaSureTM versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSureTM Vessel Sealing System in Minimally Invasive Surgery in Children" Int'L Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Stagegaard, N., Petersen H.H., Chen X., Svendsen J.H., "Indication of the Radiofrequency Induced Lesion Size by Pre-ablation Measurements" Europace (2005) 7, 525-534.
Strasberg et al., "Use of a Bipolar Vassel-Sealing Device for Parenchymal Transection During Liver Surgery" Journal of Gastrointestinal Surgery, vol. 6, No. 4, Jul /Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.-Medical Professionals: TargisTM Technology (Date Unknown). "Overcoming the Challenge" located at: <http://www.urologix.com!medicaUtechnology.html> Nov. 18, 1999; 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSureTM Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.

(56) References Cited

OTHER PUBLICATIONS

Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product Instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSureTM" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.

Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140(Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSureTM Vessel Sealing System: A Case Report" Innovations That Work, Feb. 2002.
Humphries Jr. et al., "Finite-Element Codes To Model Electrical Heating And Non-Linear Thermal Transport In Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSureTM Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSureTM Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSureTM Vessel Sealing System in Bloodless Hemorrhoidectomy" Innovations That Work, Mar. 2000.
Joseph G. Andriole M.D et al., "Biopsy Needle Characteristics Assessed in the Laboratory", Radiology 148: 659-662, Sep. 1983.
Joseph Ortenberg, "LigaSureTM System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.

(56) References Cited

OTHER PUBLICATIONS

Extended European Search Report issued in corresponding European Application No. 19159975.2 dated Jul. 12, 2019, 7 pages.
Canadian Office Action issued in corresponding Canadian Application No. 3,034,333 dated Feb. 17, 2020, 5 pages.
Australian Examination Report issued in corresponding Australian Application No. 2019201113 dated Sep. 25, 2019, 4 pages.
Australian Examination Report issued in Australian Application No. 2019201113 dated Jun. 27, 2019, 9 pages.
Canadian Office Action dated Nov. 18, 2020 issued in corresponding CA Appln. No. 3,034,333.
Canadian Office Action issued in corresponding Canadian Application No. 3,034,333 dated Jul. 29, 2021, 6 pages.

* cited by examiner

MONOPOLAR RETURN ELECTRODE GRASPER WITH RETURN ELECTRODE MONITORING

BACKGROUND

1. Technical Field

The present disclosure relates generally to electrosurgical instruments and, more particularly, to return electrodes for monopolar electrosurgical instruments.

2. Discussion of Related Art

Electrosurgical medical devices have become widely used by surgeons. Electrosurgical medical devices include various hand-held instruments, e.g., an electrosurgical pencil, which transfers radio-frequency (RF) electrical energy to a tissue site from an electrosurgical generator. Electrical current is returned to the current source via a return electrode pad positioned under a patient, or a smaller return electrode positioned in bodily contact, with or immediately adjacent to, the surgical site. The waveforms which result from the RF electrical current may be used to produce a variety of tissue effects, depending on the power applied, and the frequency used. These effects include tissue cutting, coagulation, cauterization, and/or sealing.

The effects of the electrosurgical medical devices are localized to tissue in contact with an active electrode of the electrosurgical medical device. To ensure similar effects are not experienced at the return electrode, a contact area of the return electrode with the body of a patient is maximized such that a ratio of the active electrode with tissue and the contact area of the return electrode is minimized. As this ratio increases, there is an increased likelihood that effects may be experienced at the return electrode.

SUMMARY

Accordingly, there is a need for devices that monitor the contact area of the return electrodes during a surgical procedure to reduce the likelihood of effects occurring at the return pad.

In an aspect of the present disclosure, an electrosurgical system includes a generator, a delivery device, a return device, and a return electrode monitor (REM). The delivery device is in electrical communication with the generator and has a delivery electrode configured to deliver electrosurgical energy to tissue. The return device has a first jaw member including a first return electrode and a second jaw member including a second return electrode. The first and second jaw members are configured to capture tissue between the first and second return electrodes. The REM is disposed within the generator and is in electrical communication with the first and second return electrodes to return electrosurgical energy delivered to tissue to the generator. The REM is configured to determine a size of a return contact area of the first and second return electrodes with tissue to prevent delivery of electrosurgical energy from the generator to tissue when the size of the return contact area is below a threshold size.

In aspects, the REM is configured to monitor an impedance between portion of the return device to determine the size of the return contact area. The REM may be configured to prevent delivery of electrosurgical energy from the generator when the impedance is greater than an impedance threshold. The REM has a first return post and a second return post. The impedance may be determined by a circuit extending from the first return post, extending to the return device, through tissue, and back to the second return post. The first return electrode may be connected to the first return post via a first return path and the second return electrode may be connected to the second return post via a second return path. Alternatively, the first and second return electrodes may both be connected to the first return post via the first return path.

In some embodiments, the return device includes an activation electrode positioned on the second jaw member proximal of the second return electrode. The REM may be configured to prevent delivery of electrosurgical energy from the generator to tissue unless tissue is in contact with the activation electrode and at least one of the first or second return electrodes. The first and second electrodes may be connected to a first return post of the REM via a first return path and the activation electrode may be connected to a second return post of the REM via a second return path. The REM may be configured to measure impedance between the first and second return electrodes and the activation electrode to determine when tissue is in contact with the activation electrode.

In another aspect of the present disclosure, a generator, a deliver device, a return device, and a REM. The delivery device is in electrical communication with the generator. The delivery device has a delivery electrode that is configured to deliver electrosurgical energy from the generator to tissue. The return device has a first jaw member and a second jaw member. The first jaw member includes a first return electrode and the second jaw member includes a second return electrode. The first and second jaw members are configured to capture tissue between the first and second return electrodes. The REM is in electrical communication with each of the first and second return electrodes. The REM is disposed within the generator and is in electrical communication with the first and second return electrodes to return electrosurgical energy deliver to tissue to the generator. The REM is configured to monitor impedance between portions of the return device and to prevent delivery of electrosurgical energy from the generator to tissue when the monitored impedance is greater than predetermined threshold impedance.

In aspects, the REM is configured to measure an impedance between the first and second return electrodes and an activation electrode to determine when tissue is in contact with the activation electrode. The activation electrode may be positioned on the second jaw member proximal of the second return electrode. Additionally or alternatively, the REM may be configured to measure an impedance between the first and second return electrodes.

In another aspect of the present disclosure, a method of treating tissue includes capturing a purchase of tissue, determining a size of a return contact area, preventing delivery of electrosurgical energy from a generator when the size of the return contact area is below a threshold size, and delivering electrosurgical energy from the generator when the size of the return contact area is greater than the threshold size. Capturing the purchase of tissue includes capturing the purchase between first and second jaw members of a return device. The first jaw member has a first return electrode and the second jaw member has a second return jaw member. Determining the size of the return contact area includes determining the return contact area with a REM of the generator. The electrosurgical energy may be delivered to tissue with an active electrode of the delivery device.

In aspects, determining the size of the return contact area includes measuring an impedance between the first and second return electrodes. Preventing delivery of electrosurgical energy from the generator may occur when the impedance between the first and second return electrodes is greater than an impedance threshold. The method may include determining the impedance threshold from at least one of the delivery device, the active electrode of the delivery device, or a type of tissue.

In some aspects, determining the size of the return contact area includes measuring impedance between the first and second return electrodes and an activation electrode that is disposed on the second jaw member proximal of the second return electrode. Preventing delivery of electrosurgical energy from the generator may include providing visual indicia on the delivery device and/or locking out an activation control of the delivery device.

In certain aspects, the method may include selecting a monopolar mode of the delivery device. The method may include releasing the purchase of tissue when the return contact area is below the threshold size and capturing another purchase of tissue between the first and second jaw members.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
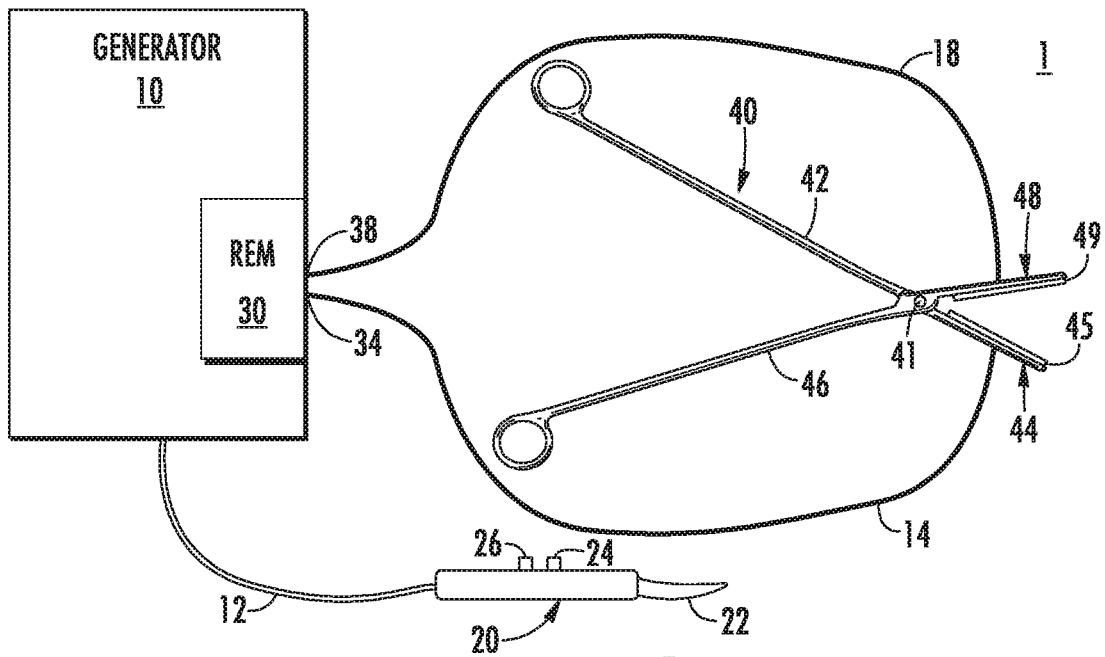
FIG. 1 is a schematic view of an electrosurgical system including a generator with a return electrode monitor and a return device provided in accordance with our present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closer to the clinician and the term "distal" refers to the portion of the device or component thereof that is farther from the clinician.

Referring now to FIG. 1, an exemplary electrosurgical system 1 is illustrated including a return device or grasper 40 provided in accordance with the present disclosure. The electrosurgical system 1 includes an electrosurgical generator 10, a delivery or monopolar device 20, and the grasper 40. The electrosurgical generator 10 is in electrical communication with the monopolar device 20 via a delivery path or conductor 12. The electrosurgical generator 10 includes a Return Electrode Monitor (REM) 30 that is in electrical communication with the grasper 40 via a first return path or conductor 14 and a second return path or conductor 18. The REM 30 is described in greater detail below.

The monopolar device 20 includes an active electrode 22 that is configured to deliver electrosurgical energy to tissue to produce a variety of effects, depending on the power of the electrosurgical energy applied and the frequency of electrosurgical energy used. These effects include surgical cutting, coagulation, cauterization, and/or sealing. The electrosurgical generator 10 may allow for the power and/or frequency of the electrosurgical energy to be manually adjusted or may automatically adjust the power and/or frequency based on a predetermined or selected desired effect. The monopolar device 20 may include a mode selection switch 24 which allows a clinician to select a desired effect during a surgical procedure. The monopolar device 20 may include an activation switch 26 that allows for selective activation of the active electrode 22 such that the active electrode 22 delivers electrosurgical energy to tissue. The active electrode 22 may have a variety of shapes including, but not limited to, a conical tip, a flat tip, a hook, a loop, and combinations thereof. When the active electrode 22 delivers electrosurgical energy to tissue, the active electrode 22 defines a delivery contact area with tissue which is the surface area of the active electrode 22 in contact with tissue. The monopolar device 20 may be an electrosurgical device having both a monopolar mode and a bipolar mode. For a detailed description of exemplary electrosurgical devices, reference may be made to U.S. Pat. No. 9,549,775, the entire contents of which are hereby incorporated by reference.

The grasper 40 includes a first arm 42 having a first jaw member 44 and a second arm 46 having a second jaw member 48. The first and second arms 42, 46 are pivotable about a pivot 41 such that the first and second jaw members 44, 48 are movable relative to one another such that tissue can be grasped therebetween. Grasper 40 may take other forms such as an endoscopic grasper having an elongated shaft extending from a handle with an end effector having first and second jaw members that are movable relative to one another. In some embodiments, one of the first or second jaw members may be fixed relative to a shaft or arm of the device.

The first jaw member 44 includes a first return electrode 45 and the second jaw member 48 includes a second return electrode 49. The first and second return electrodes 45, 49 are configured to grasp a purchase of tissue therebetween such that a return contact area is defined by portions of the first and second electrodes 45, 49 in contact with the tissue. Specifically, the first return contact area 1RA (FIG. 2) is defined by a surface area of the first electrode 45 in contact with tissue and the second return contact area 2RA (FIG. 2) is defined by a surface area of the second electrode 49 in contact with tissue. The return contact area is the sum of the first and second contact areas 1RA, 2RA.

The REM 30 is configured to monitor the return contact area of grasper 40. The REM 30 is in communication with the first return electrode 45 via the first return path 14 connected to a first return post 34 of the REM 30 and the second return electrode 48 via the second return path 18 connected to a second return post 38 of the REM 30. As shown, the first and second return paths 14, 18 are separated between the REM 30 and the first and second return electrodes 45, 49, respectively; however, the first and second return paths 14, 18 may be formed of a single cable with multiple conductors between the REM 30 and the grasper 40, i.e., with the first and second return paths 14, 18 separated from one another at the grasper 40, e.g., adjacent the first and second jaw members 44, 48.

The REM 30 is configured to determine the return contact area of the first and second electrodes 45, 49 by monitoring an impedance between the first and second return electrodes 45, 49. Specifically, the REM 30 monitors the impedance of a circuit formed from the first return post 34, through the first return path 14, through the first electrode 45, through a purchase of tissue between the first and second return electrodes 45, 49, through the second electrode 49, through the second return path 18, and to the second return post 38. The impedance between the first and second return electrodes 45, 49 is indicative of the return contact area. As a size of the return contact area is increased, the impedance between the first and second return electrodes 45, 49 decreases. As the size of the return contact area decreases, the impedance between the first and second return electrodes 45, 49 increases. The REM 30 is configured to continuously determine and monitor the size of the return contact area before and during a surgical procedure. During a surgical procedure, the REM 30 is configured to deactivate and/or prevent the delivery of electrosurgical energy to the active electrode 22 when a size of the return contact area is below a predetermined threshold. The predetermined threshold of the size of the return contact area is associated with an impedance threshold which can be monitored by the REM 30 such that when an impedance monitored by the REM 30 is greater than the impedance threshold, the REM 30 deactivates or disables the delivery of electrosurgical energy from the electrosurgical generator 10.

The impedance threshold may be based on a ratio of a size of the return contact area to a size of the delivery contact area. Specifically, as the ratio increases, the size of the return contact area increases relative to the size delivery contact area. The impedance threshold may be set at a value to ensure that the ratio is greater than a ratio limit. When the ratio is greater than the ratio limit, the size of the return contact area compared to the size of the delivery contact area is large enough to ensure that effects of electrosurgical energy delivery from the active electrode 22 are not experienced at the return electrodes, e.g., return electrodes 45, 49. In some embodiments, the ratio limit is in the range of about 10:1; however, the ratio limit may be greater or smaller than 10:1.

The impedance threshold may be determined during a surgical procedure or may be preset by the manufacturer. Additionally or alternatively, the impedance threshold may be specific to a type or shape of the active electrode 22. For example, the impedance threshold may be higher for a conical active electrode than an impedance threshold with a flat active electrode where the size of the delivery contact area may be greater. The impedance threshold may be set when the monopolar device 20 is connected to the generator 10 such that the monopolar device 20 is in electrical communication with the generator 10. Additionally or alternatively, the impedance threshold may be set when an active electrode, e.g., active electrode 22, is secured to the monopolar device 20. In addition, the impedance threshold may be set when an electrosurgical device having both monopolar and bipolar modes has the monopolar mode selected or activated.

Figure 2:
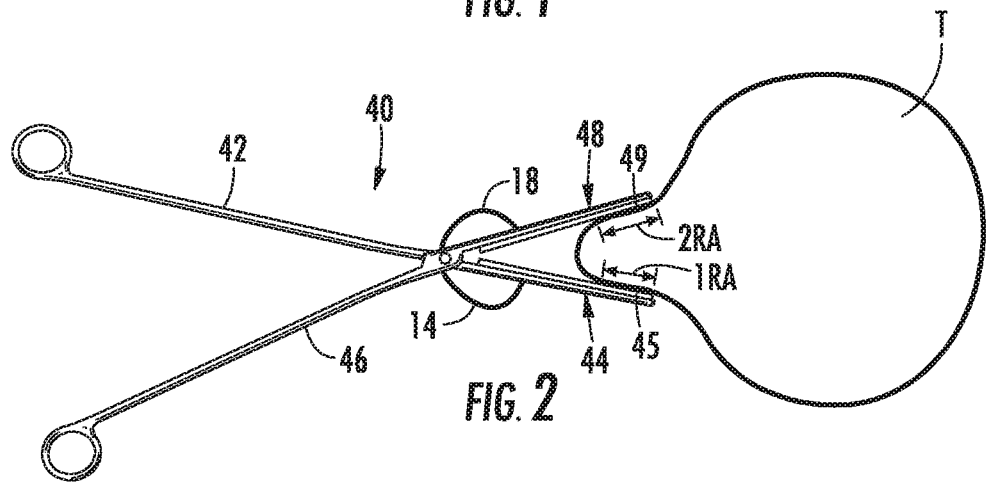
FIG. 2 is a schematic view of the return device of FIG. 1 with a first purchase of tissue between jaw members of the return device.

With reference to FIG. 2, the grasper 40 is shown with a first purchase of tissue T grasped between the first and second jaw members 44, 48 such that each of the first and second return electrodes 45, 49 have a small return contact area with the tissue T. Specifically, the first return contact area 1RA is shown along the first return electrode 45 and the second return contact area 2RA is shown along the second return electrode 49. When the tissue T is grasped as shown in FIG. 2, the impedance $\Omega$ between the first and second return electrodes 45, 49 is high and likely greater than an impedance threshold $\Omega_T$ such that the REM 30 deactivates or prevents the generator 10 from supplying electrosurgical energy to a monopolar device, e.g., monopolar device 20 (FIG. 1).

Figure 3:
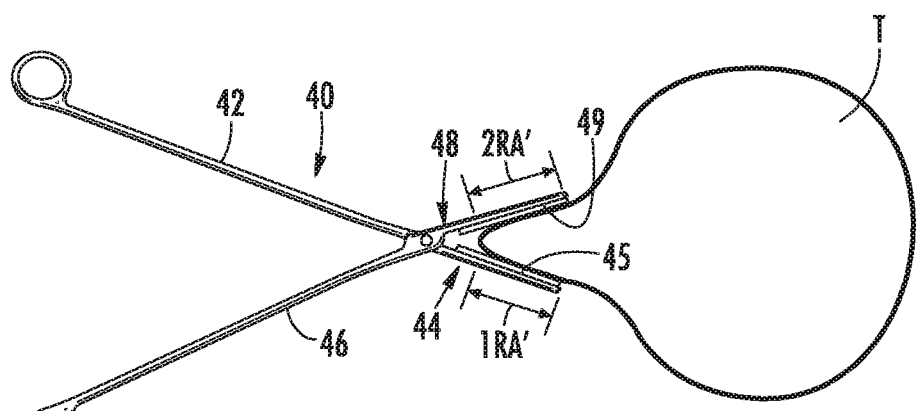
FIG. 3 is a schematic view of the return device of FIG. 1 with a second purchase of tissue between the jaw members of the return device.

With reference to FIG. 3, the grasper 40 is shown with a second purchase of tissue grasped between the first and second jaw members 44, 48 such that each of the first and second return electrodes 45, 49 have a large return contact area with the tissue T. Specifically, the first return contact area 1RA' is shown along the first return electrode 45 and the second return contact area 2RA' is shown along the second return electrode 49. When the tissue T is grasped as shown in FIG. 3, the impedance $\Omega$ between the first and second return electrodes is low and likely lower than an impedance threshold $\Omega_T$ such that the REM 30 allows for activation of the generator 10 to supply electrosurgical energy to a monopolar device, e.g., monopolar device 20 (FIG. 1).

Figure 4:
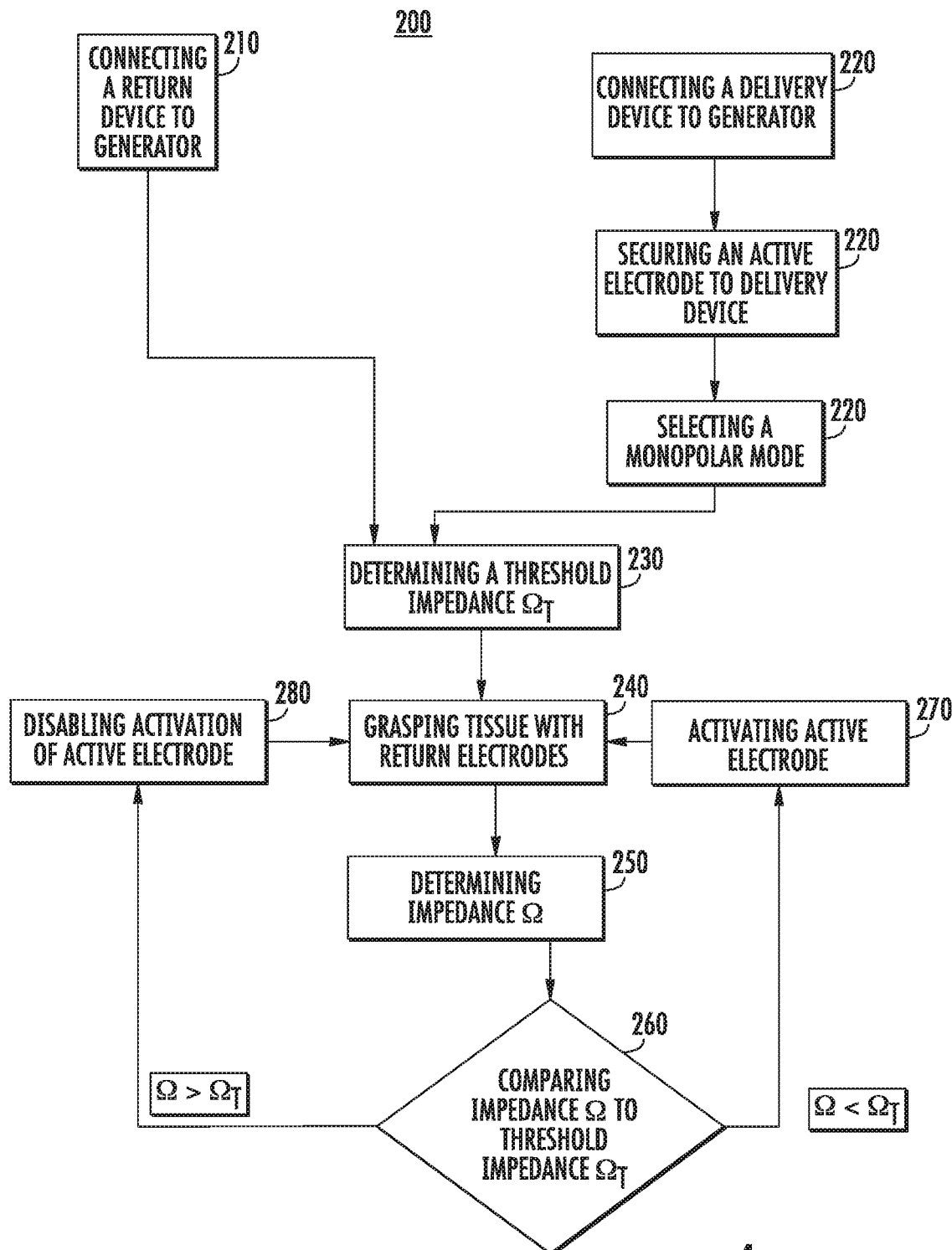
FIG. 4 is a flow chart of a method of using an electrosurgical system in accordance with the present disclosure.

Referring to FIG. 4, a method 200 of delivering electrosurgical energy to tissue with reference to the electrosurgical system 1 of FIG. 1. Initially, the return or grasping device 40 is connected to the generator 10 such that the first and second electrodes 45, 49 are in electrical communication with the REM 30 of the generator 10 by separate return paths, e.g., first and second return paths 14, 18 (Step 210). The delivery or monopolar device 20 is also connected to the generator 10 such that the monopolar device 20 is in electrical communication with the generator 10 (Step 220).

An active electrode 22 is then secured to the monopolar device 20 (Step 222). In embodiments, the active electrode 22 is selected from a plurality of active electrodes 22 based on the desired effect the active electrode 22 and/or on the type of tissue to be treated. The active electrode 22 may also be non-removable from the monopolar device 20. In some embodiments, the monopolar device 20 is selected by the active electrode 22 fixed to the monopolar device 20.

When the active electrode 22 is secured to the monopolar device 20, a monopolar mode of the monopolar device 20 is selected or activated (Step 224). The monopolar device 20 may include a mode selection switch 24 that allows a clinician to switch between a monopolar mode and a bipolar mode. In some embodiments, the monopolar device 20 is always in a monopolar mode such that when the generator 10 is activated, the monopolar mode of the monopolar device 20 is activated.

When the monopolar device 20 and the grasping device 40 are both connected to the generator 10 with the monopolar mode selected on the monopolar device 20, the REM 30 of the generator 10 determines a threshold impedance $\Omega_T$ (Step 230). The threshold impedance $\Omega_T$ may be set by a clinician or automatically determined by the REM 30 based on the active electrode 22, the geometry of the first and second return electrodes 45, 49, the type of tissue to be effected, and/or the desired effect. The grasping device 40 is then used grasp a purchase of tissue between the first and second return electrodes 45, 49 (Step 240). When the purchase of tissue is grasped between the first and second return electrodes 45, 49, the REM 30 determines the impedance Ω between the first and second return electrodes 45, 49 (Step 250). As detailed above, the impedance Ω is indicative to the size of a return contact area of the first and second return electrodes 45, 49 with the purchase of tissue. The REM 30 compares the measured impedance Ω to the threshold impedance $\Omega_T$ (Step 260).

When the impedance Ω is less than the threshold impedance $\Omega_T$, the active electrode 22 is enabled or capable of being activated (Step 270). The active electrode 22 may be activated by a clinician actuating the activation switch 26. The monopolar device 20 may provide visual indicia that the active electrode 22 is enabled, e.g., a green light may appear on the monopolar device 20. After the active electrode 22 is activated to effect tissue, the active electrode 22 is deactivated. The active electrode 22 can then be reactivated to effect tissue again, the tissue can be regrasped, or the surgical procedure may be complete.

When the impedance Ω is greater than the threshold impedance $\Omega_T$, the REM 30 deactivates or prevents the active electrode 22 from being activated (Step 280). The monopolar device 20 may provide visual indicia that the active electrode 22 is disabled, e.g., a red light may appear on the monopolar device 20. Additionally or alternatively, the activation switch 26 may be locked out such that the activation switch 26 may not be actuated to provide tactile indicia that the active electrode 22 is disabled. When the active electrode 22 is disabled, the clinician may release and grasp another purchase of tissue with the grasping device 40 (Step 240) until the REM 30 measures a new impedance Ω that is less than the threshold impedance $\Omega_T$ (Step 250).

Figure 5:
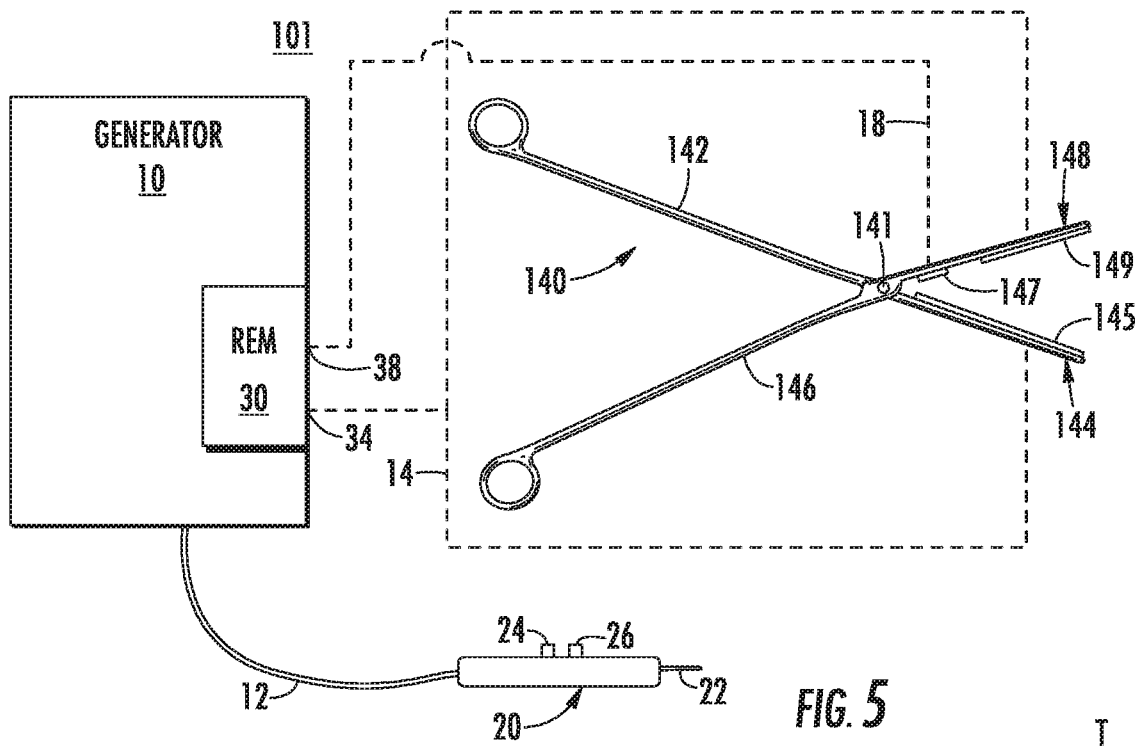
FIG. 5 is a schematic view of another electrosurgical system including a generator with a return electrode monitor and a return device provided in accordance with our present disclosure.

Referring now to FIG. 5, another exemplary electrosurgical system 101 is illustrated including a return device or grasper 140 provided in accordance with the present disclosure. Some elements of the electrosurgical system 101 are similar to elements of the electrosurgical system 1 detailed above and are represented with similar labels. As such, only the differences will be detailed herein for brevity.

The electrosurgical system includes an electrosurgical generator 10, a monopolar device 20, and the grasper 140. The electrosurgical generator 10 includes a Return Electrode Monitor (REM) 30 that is in electrical communication with the grasper 140 via a first return path or conductor 14 and a second return path or conductor 18.

The grasper 140 includes a first arm 142 having a first jaw member 144 and a second arm 146 having a second jaw member 148. The first and second arms 142, 146 are pivotable relative to one another about a pivot 141 such that the first and second jaw members 144, 148 are pivotable relative to one another. The first jaw member 144 includes a first return electrode 145. The second jaw member 148 includes a second return electrode 149 and an activation electrode 147. The activation electrode 147 is positioned proximal of the second return electrode 149 and is electrically isolated from the first and second return electrodes 145, 149.

The REM 30 is configured to determine that the return contact area of the first and second electrodes 145, 149 is sufficient to prevent effects from the active electrode 22 to be seen at the first return electrode 145, the second return electrode 149, and/or the activation electrode 147. The REM 30 utilizes the activation electrode 147 to determine when a return contact area of a purchase of tissue grasped between the first and second return electrodes 145, 149 is large enough such that a ratio of the return contact area to a delivery contact area is greater than a ratio limit, e.g., about 10:1.

The REM 30 determines the return contact area is sufficient by monitoring the impedance Ω between the first and second electrodes 145, 149 and the activation electrode 147. The first and second electrodes 145, 149 are in electrical communication with one another through the return path 14 which is connected to the first post 34 of the REM 30. The activation electrode 147 is connected to the second post 38 of the REM 30 by the second return path 18.

Figure 6:
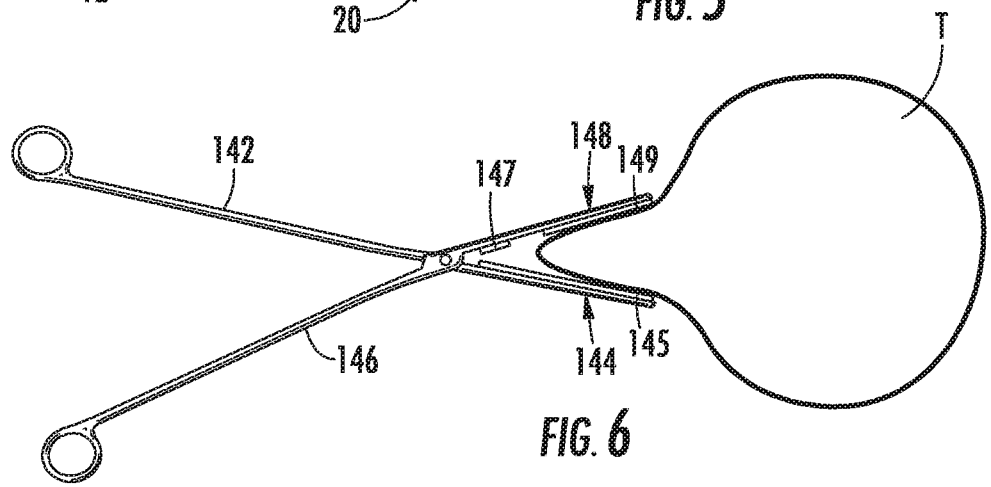
FIG. 6 is a schematic view of the return device of FIG. 5 with a first purchase of tissue between jaw members of the return device.

With reference to FIG. 6, when a purchase of tissue T is grasped between the first and second jaw members 144, 148 such that the tissue T does not reach the activation electrode 147, an impedance Ω between the activation electrode 147 and the first and second return electrodes 145, 149 is extremely large and may not be measurable, i.e., approaching infinity. In such situations, the impedance Ω is greater than an impedance threshold $\Omega_T$ such that the REM 30 deactivates or prevents the generator 10 from supplying electrosurgical energy to a monopolar device, e.g., monopolar device 20 (FIG. 5).

Figure 7:
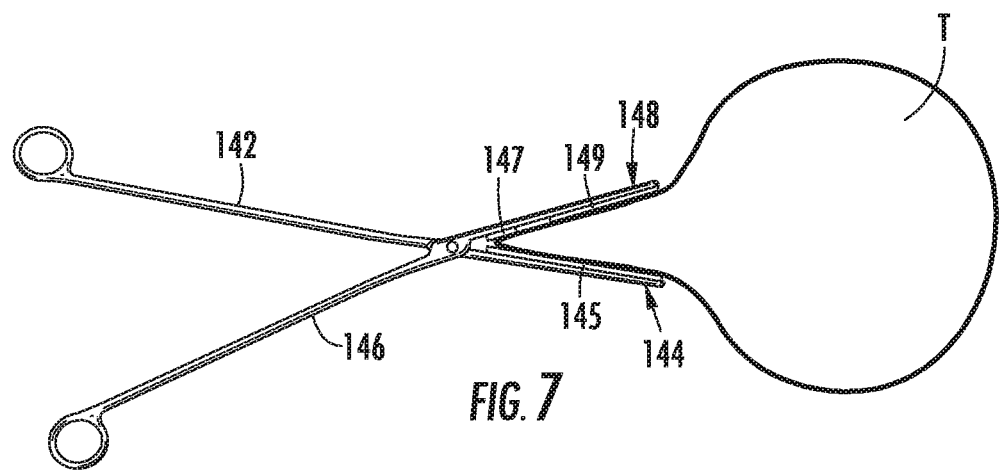
FIG. 7 is a schematic view of the return device of FIG. 6 with a second purchase of tissue between the jaw members of the return device.

With reference to FIG. 7, when a purchase of tissue T is grasped between the first and second jaw members 144, 148 such that the tissue T reaches and is in contact with the activation electrode 147, an impedance Ω between the activation electrode 147 and the first and second return electrodes 145, 149 is significantly less than the impedance Ω measured when the activation electrode 147 is not contacted. When the REM 30 determines that the tissue T is in contact with the activation electrode 147, the REM 30 allows for activation of the generator 10 to supply electrosurgical energy to a monopolar device, e.g., monopolar device 20 (FIG. 5).

When the grasper 140 includes the activation electrode 147, the impedance threshold $\Omega_T$ for the system 101 can be higher than the impedance threshold $\Omega_T$ for the system 1 since the impedance Ω difference between non-contact with the activation electrode 147 and contact with the activation electrode 147 is significantly greater than when the return contact area is greater than a ratio limit as shown in FIG. 2.

A method of using the system 101 is substantially similar to the method 200 and will not be detailed herein for brevity.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 8:
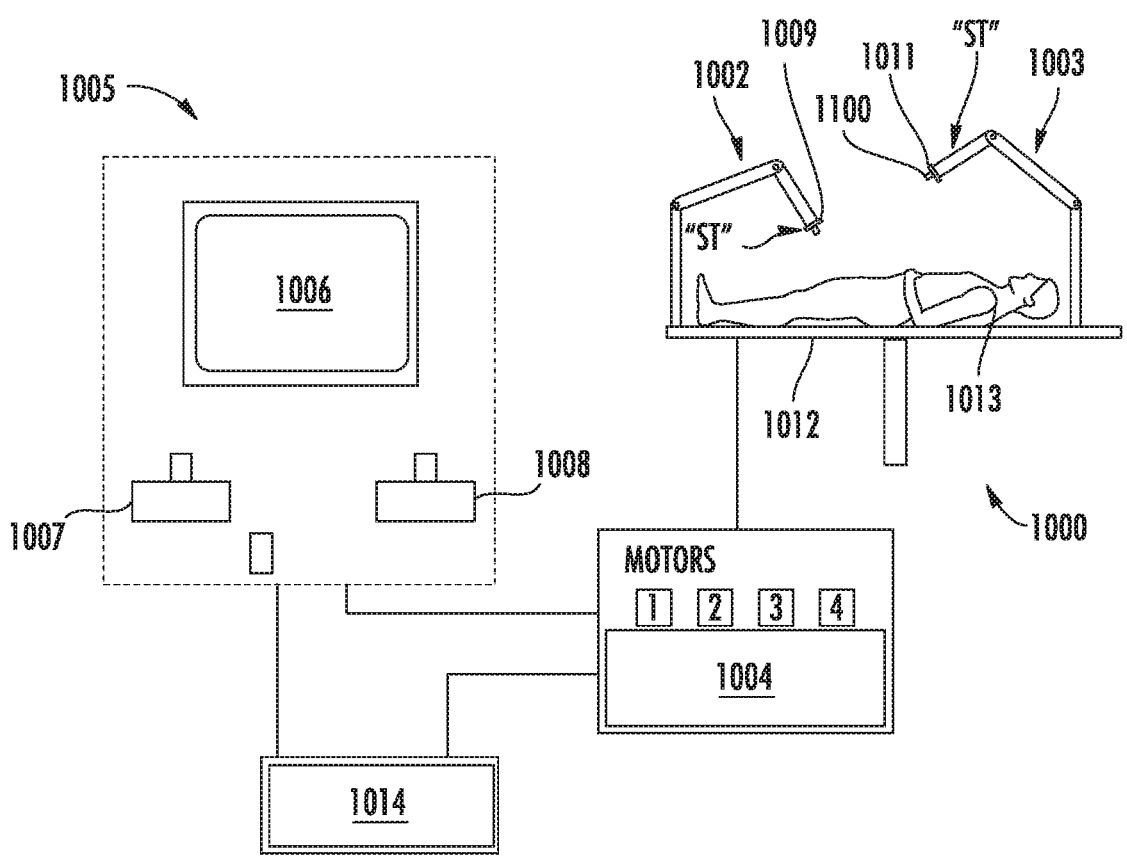
FIG. 8 is a schematic view of a robotic surgical system provided in accordance with the present disclosure.

Turning to FIG. 8, a robotic surgical system configured for use in accordance with the present disclosure is shown generally identified by reference numeral 1000. Aspects and features of robotic surgical system 1000 not germane to the understanding of the present disclosure are omitted to avoid obscuring the aspects and features of the present disclosure in unnecessary detail.

Robotic surgical system 1000 generally includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person, e.g., a surgeon, may be able to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and an attaching device 1009, 1011, to which may be attached, for example, a surgical tool "ST." One or more of the surgical tools "ST" may include a DLU, e.g., DLU 100, similar to those detailed above, thus providing such functionality on a robotic surgical system 1000.

Robot arms 1002, 1003 may be driven by electric drives, e.g., motors, connected to control device 1004. Control device 1004, e.g., a computer, may be configured to activate the motors, in particular by means of a computer program, in such a way that robot arms 1002, 1003, their attaching devices 1009, 1011, and, thus, the surgical tools "ST" execute a desired movement and/or function according to a corresponding input from manual input devices 1007, 1008, respectively. Control device 1004 may also be configured in such a way that it regulates the movement of robot arms 1002, 1003 and/or of the motors. The surgical tools "ST" may include optical-based sealing instruments configured to seal and/or cut tissue without a mechanical blade detailed above.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. An electrosurgical system, comprising:
a generator;
a delivery device in electrical communication with the generator, the delivery device having a delivery electrode configured to deliver electrosurgical energy from the generator to tissue, the delivery electrode defining a delivery contact area having a size based on a surface area of the delivery electrode in contact with the tissue;
a return device having a first jaw member and a second jaw member, the first jaw member including a first return electrode and the second jaw member including a second return electrode, the first and second jaw members configured to capture the tissue between the first and second return electrodes; and
a return electrode monitor in electrical communication with each of the first and second return electrodes, the return electrode monitor disposed within the generator and in electrical communication with the first and second return electrodes to return the electrosurgical energy delivered to the tissue to the generator, the return electrode monitor configured to determine a size of a return contact area of the first and second return electrodes with the tissue and to prevent delivery of the electrosurgical energy from the generator to the tissue by deactivating the generator when the size of the return contact area is below a threshold size, wherein the threshold size is determined based on a ratio of the size of the return contact area to the size of the delivery contact area.

2. The electrosurgical system according to claim 1, wherein the return electrode monitor is configured to monitor an impedance between portions of the return device to determine the size of the return contact area, the return electrode monitor configured to prevent delivery of the electrosurgical energy from the generator when the impedance is greater than an impedance threshold.

3. The electrosurgical system according to claim 2, wherein the return electrode monitor has a first return post and a second return post, the impedance being determined by a circuit extending from the first return post, extending to the return device, through the tissue, and back to the second return post.

4. The electrosurgical system according to claim 3, wherein the first return electrode is connected to the first return post via a first return path and the second return electrode is connected to the second return post via a second return path.

5. The electrosurgical system according to claim 3, wherein the first and second return electrodes are both connected to the first return post via a first return path.

6. The electrosurgical system according to claim 1, wherein the return device includes an activation electrode positioned on the second jaw member proximal of the second return electrode.

7. The electrosurgical system according to claim 6, wherein the return electrode monitor is configured to prevent delivery of the electrosurgical energy from the generator to the tissue unless the tissue is in contact with the activation electrode and at least one of the first return electrode or the second return electrode.

8. The electrosurgical system according to claim 6, wherein the first and second return electrodes are connected to a first return post of the return electrode monitor via a first return path and the activation electrode is connected to a second return post of the return electrode monitor via a second return path.

9. The electrosurgical system according to claim 8, wherein the return electrode monitor is configured to measure an impedance between the first and second return electrodes and the activation electrode to determine when the tissue is in contact with the activation electrode.

10. An electrosurgical system, comprising:
a generator;
a delivery device in electrical communication with the generator, the delivery device having a delivery electrode configured to deliver electrosurgical energy from the generator to tissue, the delivery electrode defining a delivery contact area having a size based on a surface area of the delivery electrode in contact with the tissue;
a return device having a first jaw member and a second jaw member, the first jaw member including a first return electrode and the second jaw member including a second return electrode, the first and second jaw members configured to capture the tissue between the first and second return electrodes; and
a return electrode monitor in electrical communication with each of the first and second return electrodes, the return electrode monitor in electrical communication with the first and second return electrodes to return the electrosurgical energy delivered to the tissue to the generator, the return electrode monitor configured to monitor a size of a return contact area of the first and second return electrodes with the tissue and to prevent delivery of the electrosurgical energy from the generator to the tissue by deactivating the generator when the size of the return contact area is below a threshold size, wherein the threshold size is determined based on a ratio of the size of the return contact area to the size of the delivery contact area.

11. A method of treating tissue, the method comprising:
capturing a purchase of tissue between first and second jaw members of a return device, the first jaw member having a first return electrode and the second jaw member having a second return electrode;
delivering electrosurgical energy, by a delivery device having a delivery electrode, to a delivery contact area of the purchase of tissue, the delivery contact area having a size based on a surface area of the delivery electrode in contact with the purchase of tissue;
determining a size of a return contact area of the purchase of the tissue with a return electrode monitor of a generator;
preventing delivery of electrosurgical energy from the generator by deactivating the generator, with the return electrode monitor, when the size of the return contact area is below a threshold size, wherein the threshold size is determined based on a ratio of the size of the return contact area to the size of the delivery contact area; and
delivering the electrosurgical energy from the generator to the tissue with an active electrode of a delivery device when the size of the return contact area is greater than the threshold size.

12. The method according to claim 11, wherein determining the size of the return contact area includes measuring an impedance between the first and second return electrodes.

13. The method according to claim 12, wherein preventing delivery of the electrosurgical energy from the generator occurs when the impedance between the first and second return electrodes is greater than an impedance threshold.

14. The method according to claim 13, further comprising determining the impedance threshold from at least one of the delivery device, the active electrode of the delivery device, or a type of the tissue.

15. The method according to claim 11, wherein determining the size of the return contact area includes measuring an impedance between the first and second return electrodes and an activation electrode disposed on the second jaw member proximal of the second return electrode.

16. The method according to claim 11, wherein preventing delivery of the electrosurgical energy from the generator includes providing visual indicia on the delivery device.

17. The method according to claim 11, further comprising selecting a monopolar mode of the delivery device.

18. The method according to claim 11, further comprising:
releasing the purchase of tissue when the return contact area is below the threshold size; and
capturing another purchase of tissue between the first and second jaw members.

* * * * *